US009478019B2

(12) United States Patent
Sezginer et al.

(10) Patent No.: US 9,478,019 B2
(45) Date of Patent: Oct. 25, 2016

(54) RETICLE INSPECTION USING NEAR-FIELD RECOVERY

(71) Applicant: KLA-Tencor Corporation, Miliptas, CA (US)

(72) Inventors: Abdurrahman Sezginer, Monte Sereno, CA (US); Rui-fang Shi, Cupertino, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

(21) Appl. No.: 14/702,336

(22) Filed: May 1, 2015

(65) Prior Publication Data
US 2015/0324963 A1 Nov. 12, 2015

Related U.S. Application Data

(60) Provisional application No. 61/988,909, filed on May 6, 2014, provisional application No. 62/054,185, filed on Sep. 23, 2014.

(51) Int. Cl.
*G06T 7/00* (2006.01)
*G01N 21/88* (2006.01)
(Continued)

(52) U.S. Cl.
CPC ............. *G06T 7/00* (2013.01); *G01N 21/8851* (2013.01); *G01N 21/9501* (2013.01); *G01N 21/956* (2013.01); *G01N 21/95607* (2013.01); *G06T 7/001* (2013.01); *G06T 7/0008* (2013.01);
(Continued)

(58) Field of Classification Search
None
See application file for complete search history.

(56) References Cited

U.S. PATENT DOCUMENTS 5,795,688 A * 8/1998 Burdorf ........... G01N 21/95607
356/237.1
6,578,188 B1 * 6/2003 Pang ..................... G03F 1/26
716/52
(Continued)

FOREIGN PATENT DOCUMENTS

JP 2004-157518 6/2004
JP 2005-538425 12/2005
(Continued)

OTHER PUBLICATIONS

Howard et al., "Production Evaluation of Automated Reticle Defect Printability Prediction Application," Mask and Lithography Conference (EMLC) 2007 23rd European, Jan. 22-26, 2007, pp. 1-7.
(Continued)

*Primary Examiner* — David F Dunphy
(74) *Attorney, Agent, or Firm* — Ann Marie Mewherter

(57) ABSTRACT

Systems and methods for detecting defects on a reticle are provided. The embodiments include generating and/or using a data structure that includes pairs of predetermined segments of a reticle pattern and corresponding near-field data. The near-field data for the predetermined segments may be determined by regression based on actual image(s) of a reticle generated by a detector of a reticle inspection system. Inspecting a reticle may then include separately comparing two or more segments of a pattern included in an inspection area on the reticle to the predetermined segments and assigning near-field data to at least one of the segments based on the predetermined segment to which it is most similar. The assigned near-field data can then be used to simulate an image that would be formed for the reticle by the detector, which can be compared to an actual image generated by the detector for defect detection.

41 Claims, 2 Drawing Sheets

(51) Int. Cl.
*G01N 21/956* (2006.01)
*G01N 21/95* (2006.01)

(52) U.S. Cl.
CPC ............ *G01N2021/8887* (2013.01); *G01N 2021/95676* (2013.01); *G01N 2201/06113* (2013.01); *G01N 2201/10* (2013.01); *G01N 2201/12* (2013.01); *G06T 2207/10056* (2013.01); *G06T 2207/30148* (2013.01)

(56) References Cited

U.S. PATENT DOCUMENTS

| | | |
|---|---|---|
| 6,902,855 B2 | 6/2005 | Peterson et al. |
| 7,418,124 B2 | 8/2008 | Peterson |
| 7,570,796 B2 | 8/2009 | Zafar et al. |
| 7,646,906 B2 | 1/2010 | Saidin et al. |
| 7,676,077 B2 | 3/2010 | Kulkarni et al. |
| 7,769,225 B2 | 8/2010 | Kekare et al. |
| 7,820,341 B2 | 10/2010 | Laidig et al. |
| 7,873,204 B2 | 1/2011 | Wihl et al. |
| 7,932,004 B1 | 4/2011 | Xiong et al. |
| 7,995,832 B2 | 8/2011 | Xiong et al. |
| 8,102,408 B2 | 1/2012 | Verma et al. |
| 8,594,823 B2 | 11/2013 | Park et al. |
| 2002/0019729 A1* | 2/2002 | Chang ............... G03F 1/26 703/6 |
| 2005/0244728 A1* | 11/2005 | Liu ............... G03F 1/144 430/5 |
| 2006/0051682 A1 | 3/2006 | Hess et al. |
| 2006/0236294 A1 | 10/2006 | Saidin et al. |
| 2006/0273266 A1* | 12/2006 | Preil ............... G03F 1/84 250/548 |
| 2009/0016595 A1 | 1/2009 | Peterson et al. |
| 2009/0297019 A1 | 12/2009 | Zafar et al. |
| 2011/0276935 A1 | 11/2011 | Fouquet et al. |
| 2011/0299759 A1 | 12/2011 | Shi et al. |
| 2012/0121160 A1* | 5/2012 | Matsuoka ............... H01J 37/28 382/145 |
| 2013/0058558 A1 | 3/2013 | Ueno et al. |
| 2013/0111417 A1* | 5/2013 | Hess ............... G01N 21/9501 716/51 |
| 2013/0236083 A1 | 9/2013 | Wang et al. |
| 2015/0054940 A1 | 2/2015 | Shi et al. |
| 2015/0228063 A1* | 8/2015 | Minakawa ............ H01J 37/244 382/151 |

FOREIGN PATENT DOCUMENTS

| | | | |
|---|---|---|---|
| WO | WO 2006/019919 | * 2/2006 | ............ G03F 1/14 |
| WO | 2013/142079 | 9/2013 | |

OTHER PUBLICATIONS

International Search Report for PCT/US2015/029072 mailed Jul. 31, 2015.
Wang, Z. et al., "Spatial light interference microscopy (SLIM)," Optics Express, vol. 19, No. 2, Jan. 2011, pp. 1016-1026.

* cited by examiner

RETICLE INSPECTION USING NEAR-FIELD RECOVERY

BACKGROUND OF THE INVENTION

1. Field of the Invention

The present invention generally relates to systems and methods for reticle inspection using near-field recovery.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing (CMP), etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on reticles to promote higher yield in the manufacturing process and thus higher profits. Inspection has always been an important part of fabricating semiconductor devices such as ICs. However, as the dimensions of semiconductor devices decrease, inspection becomes even more important to the successful manufacture of semiconductor devices.

Existing methods for reticle inspection utilize one of a number of imaging modes to inspect a mask. The most common inspection mode known as reticle plane inspection (RPI) involves capturing high resolution transmitted and reflected images of a reticle and processing the two images together. Another inspection method called low numerical aperture (NA) inspection (LNI) involves a mode that emulates the wafer scanner optical conditions, capturing one image in transmitted light at a lower NA than RPI with illumination conditions that approximate the scanner's. Another method for contamination inspection known as SL involves analyzing two images, RPI transmitted and reflected, to find defects that standout from the background pattern.

Many reticle inspection methods detect defects on reticles using die-to-database type comparisons. Such inspection typically involves acquiring a microscope image of a reticle. From a database that describes the intended pattern on the reticle, an image that the inspection microscope is expected to observe of that reticle may be calculated or simulated. The acquired optical image may then be compared to the calculated or simulated image to detect defects on the reticle.

Calculating a reticle image as described above may include calculating the diffraction of light by the reticle. Maxwell's equations completely and accurately describe the diffraction of electromagnetic waves by a reticle. However, there is no practical method of solving Maxwell's equations accurately for an entire reticle in the required inspection time, which is one to two hours. Some currently used methods use approximations such as the Kirchhoff approximation to estimate the diffracted field. However, this limits the accuracy of the calculated image and therefore limits the smallest defect that can be detected.

Advancement in optical proximity correction (OPC) results in ever-increasing complexity in the patterns written on a photomask or reticle. Reticle inspection is typically performed using a sophisticated optical microscope such as those described above with advanced algorithms to qualify the written patterns. It becomes more and more difficult to separate critical (printing) defects from non-critical (nuisance) defects due to the OPC complexity. The traditional methods to address this issue are: (a) to utilize empirical rules based on shape and size of the defect for manual disposition, (b) to build empirical rules and automatic defect classification (ADC) software to disposition large numbers of defects automatically, and (c) to use an aerial imaging tool to acquire optical images under the proper lithography conditions to disposition defects.

There are, however, a number of disadvantages of such currently used methods and systems. For example, currently used methods require manual defect disposition by a user to review the defects one-by-one. Increased OPC complexity means oftentimes the user has difficulty separating the printing defects from non-printing defects with a few empirical rules. In addition, potentially large numbers of defects can overload the user and prevent finishing the defect disposition in a reasonable time period. Rule-based methods are not directly related to the printability of a defect. Increased OPC complexity with inverse lithography technology (ILT) can limit the usefulness of the method. In addition, aerial imaging tools utilize a combination of hardware and algorithms to mimic the scanner vector imaging effect. However, the accuracy of such tools is never fully independently verified. More critically, such methods do not consider the complex photoresist development or etching process after imaging is done on a scanner. Studies have shown that there is a poor correlation between the defect size measured on an aerial imaging tool and that measured on a wafer.

Accordingly, it would be advantageous to develop methods and/or systems for reticle inspection that do not have one or more of the disadvantages described above.

SUMMARY OF THE INVENTION

The following description of various embodiments is not to be construed in any way as limiting the subject matter of the appended claims.

One embodiment relates to a computer-implemented method for detecting defects on a reticle. The method includes separating a pattern included in an inspection area on the reticle into two or more segments and separately comparing the two or more segments to predetermined segments included in a data structure. The data structure includes pairs of the predetermined segments of a reticle pattern and corresponding near-field data. The method also includes assigning near-field data to at least one of the two or more segments based on one of the predetermined segments to which the at least one of the two or more segments is most similar. In addition, the method includes generating near-field data for the inspection area based on the assigned near-field data and simulating an image, based on the generated near-field data, of the inspection area that would be formed by a detector of a reticle inspection system. The method further includes acquiring an actual image of the inspection area on a physical version of the reticle generated by the detector and detecting defects on the reticle by comparing the simulated image to the actual image. The separating, separately comparing, assigning, generating, simulating, acquiring, and detecting steps are performed with one or more computer systems.

Each of the steps of the computer-implemented method may be further performed as described herein. In addition, the computer-implemented method may include any other step(s) of any other method(s) described herein. Furthermore, the computer-implemented method may be performed by any of the systems described herein.

Another embodiment relates to a non-transitory computer-readable medium storing program instructions executable on a computer system for performing a computer-implemented method for detecting defects on a reticle. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

An additional embodiment relates to a system configured to detect defects on a reticle. The system includes a reticle inspection subsystem that includes a detector configured to generate an actual image of an inspection area on a physical version of the reticle. The system also includes one or more computer subsystems configured for performing the separating, separately comparing, assigning, generating, simulating, acquiring, and detecting steps of the method described above. The system may be further configured as described herein.

A further embodiment relates to a computer-implemented method for setting up a reticle inspection process. The method includes separating pattern information for a reticle into predetermined segments. The method also includes determining near-field data for the predetermined segments based on one or more actual images of the reticle acquired by a detector of a reticle inspection system. The near-field data for the predetermined segments is determined by regression based on the one or more actual images of the reticle. In addition, the method includes generating a data structure that includes pairs of the predetermined segments and the near-field data corresponding to the predetermined segments. The method further includes setting up the reticle inspection process by incorporating information for the generated data structure in a recipe for the reticle inspection process such that during the reticle inspection process, two or more segments in an inspection area on the reticle or another reticle are compared to the predetermined segments and the near-field data for one of the predetermined segments to which at least one of the two or more segments is most similar is assigned to the at least one of the two or more segments. The separating, determining, generating, and setting up steps are performed by one or more computer systems.

Each of the steps of the computer-implemented method may be further performed as described herein. In addition, the computer-implemented method may include any other step(s) of any other method(s) described herein. Furthermore, the computer-implemented method may be performed by any of the systems described herein.

Yet another embodiment relates to another computer-implemented method for setting up a reticle inspection process. The method includes separating pattern information for a reticle into predetermined segments. The method also includes determining near-field data for the predetermined segments by numerically solving equations that govern electromagnetic fields for the predetermined segments. In addition, the method includes generating a data structure that includes pairs of the predetermined segments and the near-field data corresponding to the predetermined segments. The method further includes setting up the reticle inspection process by incorporating information for the generated data structure in a recipe for the reticle inspection process such that during the reticle inspection process, two or more segments in an inspection area on the reticle or another reticle are compared to the predetermined segments and the near-field data for one of the predetermined segments to which at least one of the two or more segments is most similar is assigned to the at least one of the two or more segments. The separating, determining, generating, and setting up steps are performed by one or more computer systems.

Each of the steps of the computer-implemented method may be further performed as described herein. In addition, the computer-implemented method may include any other step(s) of any other method(s) described herein. Furthermore, the computer-implemented method may be performed by any of the systems described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

Figure 1:
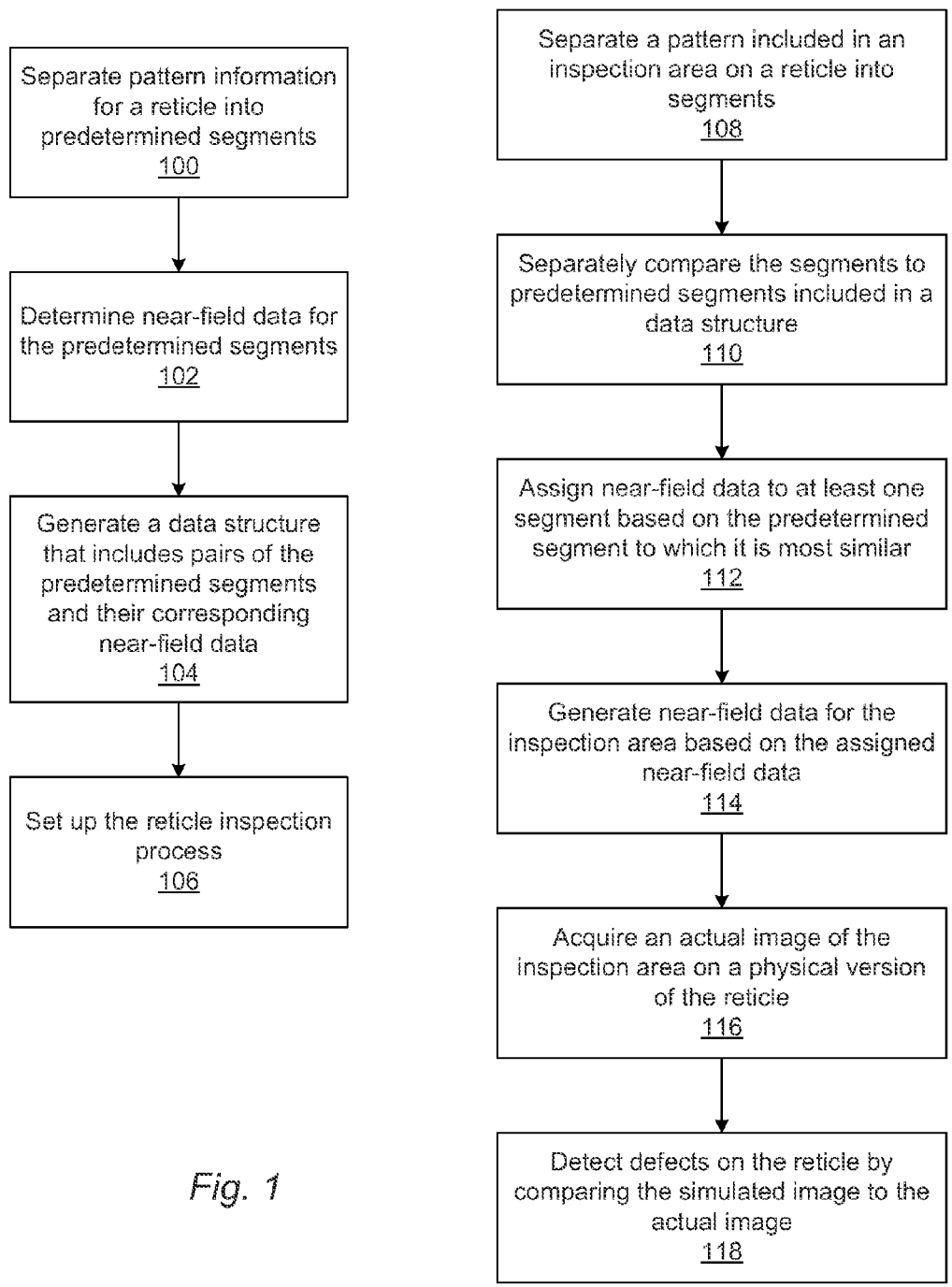
FIG. 1 is a flow chart illustrating an embodiment of a computer-implemented method for setting up a reticle inspection process and an embodiment of a computer-implemented method for detecting defects on a reticle.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

The embodiments described herein generally relate to inspecting reticles by making use of a database that describes the reticle pattern. For example, as described further herein, the embodiments may be used for die-to-database inspection of reticles using near-field recovery. The embodiments described herein may be used for inspecting reticles for pattern defects and contamination.

The terms "reticle," "mask," and "photomask" are used interchangeably herein and are intended to mean any reticle or mask known in the art that is used to transfer a pattern to another substrate such as a wafer.

A "substantially high resolution image" as that term is commonly used in the art of reticle inspection refers to an image of a reticle in which features printed on the reticle appear substantially as they are formed on the reticle (within the optical limitations of the reticle inspection system used to generate the image). For example, a "substantially high resolution image" of a reticle is an image that is generated by imaging the physical reticle at the reticle plane with a substantially high resolution reticle inspection system (e.g., a reticle inspection system capable of generating images with a substantially high numerical aperture (e.g., a numerical aperture (NA) of greater than 0.8)). In contrast, a "substantially low NA" used to generate an image of a reticle may be an NA that is less than 0.5. In addition, the "substantially low NA" used to generate a reticle image may be substantially the same as the NA on the reticle side that is used by an exposure system to project an image of the reticle onto a wafer thereby transferring features on the reticle onto the wafer. Therefore, in the substantially low NA image (or LNI), the reticle features may appear substantially differently than they were formed on the reticle. For example, in an LNI, reticle features may appear to have more rounded corners than what was formed on the reticle.

The terms "design" and "design data" as used herein generally refer to the physical design (layout) of an IC and data derived from the physical design through complex simulation or simple geometric and Boolean operations. The design may be stored in a data structure such as a GDS file, any other standard machine-readable file, any other suitable file known in the art, and a design database. A GDSII file is one of a class of files used for the representation of design layout data. Other examples of such files include GL1 and OASIS files. The design used in the embodiments described herein may be stored in any of this entire class of files irrespective of data structure configuration, storage format, or storage mechanism. In addition, the pattern information for a reticle described further herein may be stored in a database that describes the reticle pattern. This reticle pattern is the pattern that can be expected on a reticle when the mask writing operation is flawless. The database may contain coordinates of vertices of polygons or may be a gray scale image.

The design may include any other design data or design data proxies described in commonly owned U.S. Pat. No. 7,570,796 issued on Aug. 4, 2009 to Zafar et al. and U.S. Pat. No. 7,676,077 issued on Mar. 9, 2010 to Kulkarni et al., both of which are incorporated by reference as if fully set forth herein. In addition, the "design" and "design data" described herein refers to information and data that is generated by a semiconductor device designer in a design process and is therefore available for use in the embodiments described herein well in advance of printing of the design on any physical reticles and/or wafers.

One embodiment relates to a computer-implemented method for setting up a reticle inspection process. As shown in step 100 of FIG. 1, the method includes separating pattern information for a reticle into predetermined segments. The terms "portion," "section," and "segment" of a reticle all refer to a set of points in the two-dimensional (2D) plan view of the reticle. Although these terms can be defined to have the same meaning, each is reserved for a conceptually distinct object in this document.

In one embodiment, diameters of the predetermined segments are larger than an optical proximity distance for the reticle. For example, as described above, the pattern information may be separated into relatively small segments or sections. Then, as described further herein, a match for segments of a database for a reticle being inspected may be searched for among the predetermined segments. To increase the probability of finding a match, the predetermined segments may be selected as relatively small sections of the database. However, the diameter of the predetermined segments should be larger than the optical proximity distance to ensure that the predetermined segments include enough pattern information so that matches can be found with a reasonable degree of confidence.

In one embodiment, the pattern information is acquired from design data for the reticle. The design data for the reticle may be stored in a database such as that described above. In some such embodiments, the method may include acquiring a database of the pattern of the reticle. The database may be acquired in any suitable manner from any suitable storage medium.

In another embodiment, the method includes selecting the predetermined segments from the pattern information based on number of instances of the predetermined segments in an entirety of the pattern for the reticle. For example, using the database, a portion of the reticle that is representative of the pattern on the rest of the reticle or another reticle can be selected.

As shown in step 102 of FIG. 1, the method also includes determining near-field data for the predetermined segments based on one or more actual images of the reticle acquired by a detector of a reticle inspection system. For example, the method may include electronically acquiring one or more optical microscope images of the selected portion of the reticle. The detector and the reticle inspection system that acquire the one or more actual images may be configured as described further herein. The images may be optical LNI images of the reticle. The one or more actual images of the reticle will be used to determine the near-field data. In this manner, the near-field may be recovered from optical LNI images. The near field of a reticle can be generally defined as the electric field at a plane arbitrarily close to the reticle. As such, the embodiments described herein may include recovering a mask near-field from images acquired with a microscope.

As described further herein, that near-field data will then be used for the reticle or another reticle to simulate a detector image for the reticle or the other reticle that will be used for defect detection for that reticle or other reticle. Therefore, the one or more actual images of the reticle that the near-field data determination may be based on are preferably acquired with the detector of the reticle inspection system that will be used for inspection of the reticle or the other reticle or a similarly configured detector of a similarly configured reticle inspection system (e.g., a different reticle inspection system of the same make and model as the reticle inspection system that will be used for inspection). In other words, since the near-field data will be used to simulate detector images, as described further herein, the actual image(s) that may be used to determine the near-field data are preferably acquired under the same optical conditions as will be used for inspection. In this manner, the interaction of the reticle with the illuminating electromagnetic waves may be measured as directly as possible using the actual reticle or another reticle. However, if the optical conditions that will be used for reticle inspection cannot be used to acquire the actual image(s) that are used to determine the near-field, the actual image(s) could be modified in some manner to simulate the actual image(s) for the reticle that would be acquired for the reticle with the inspection optical conditions. Those modified image(s) could then be used to determine the near-field data.

If a reticle other than the one that will be inspected is used to acquire the image(s) from which the near-field data is determined, the other reticle should have characteristic(s) that are substantially similar to the reticle to be inspected. For example, the reticle and the other reticle are preferably made up of substantially the same materials having substantially the same thicknesses and compositions. In addition, the two reticles may have been formed using the same processes. The two reticles may not necessarily have the same patterns printed thereon as long as the patterns on the reticles can be broken up into segments that are substantially the same (e.g., lines having similar widths, etc.). In addition, the reticle that will be inspected and the reticle that is used to acquire the images may be one and the same reticle.

The near-field data for the predetermined segments may be determined by regression based on the one or more actual images of the reticle. For example, the near-field of the selected portion of the reticle can be recovered (regressed) from its acquired optical image(s) or intensity of image(s) recorded at a detector plane. In particular, recovering the near-field of a reticle from its intensity image(s) is an inverse problem or a regression problem. Like in most inverse problems, the near-field can be recovered iteratively by minimizing a cost function (e.g., energy or penalty function). The quantity that is minimized can be the sum of squared differences between an optical image and an intensity image at the detector that is calculated from the near-field. In addition, any other suitable regression method and/or algorithm may be used to determine the near-field data from the one or more actual images.

In one embodiment, the one or more actual images of the reticle or another reticle are acquired at more than one focus setting by the detector or another detector. In this manner, in a preferred implementation, the images may be acquired at more than one focus setting (i.e., multiple focus settings). Recovery of the near-field is robust if images at more than one focus setting are used. Image(s) of a reticle can be acquired at more than one focus setting of a detector as described further herein using a system as described further herein.

In one embodiment, the regression includes a Hopkins phase approximation. In another embodiment, the regression does not include thin-mask approximations. In an additional embodiment, the regression does not include Kirchhoff approximations. For example, the near-field of the reticle is the electromagnetic field that is present at the surface of the reticle when it is illuminated by a normally-incident plane wave. In lithography and inspection, a reticle is illuminated by plane-waves that are incident from many directions. When the direction of incidence changes, according to the Hopkins approximation, the directions of the diffraction orders change but their amplitudes and phases remain approximately unchanged. The embodiments described herein can use the Hopkins' phase approximation but do not make the so-called thin-mask or Kirchhoff approximations.

As shown in step 104 of FIG. 1, the method further includes generating a data structure that includes pairs of the predetermined segments and the near-field data corresponding to the predetermined segments. In some embodiments, the data structure may be configured as a library. In this manner, the method may include forming a library that contains pairs of a segment of the database and the near-field over the corresponding segment of the reticle. In other words, the library may contain relatively small clips of reticle patterns and the associated reticle near-field. As such, reticle pattern clips and near-fields can be saved in the library as paired objects. However, the data structure may have any other suitable file format known in the art. In addition, although the data structure may be referred to as a "library" in the description provided herein, it is to be understood that no embodiments described herein require that the data structure be configured as a library. The library may therefore be generated before a reticle (or a second reticle) is inspected.

As shown in step 106 of FIG. 1, the method also includes setting up the reticle inspection process by incorporating information for the generated data structure in a recipe for the reticle inspection process such that during the reticle inspection process, two or more segments in an inspection area on the reticle or another reticle are compared to the predetermined segments and the near-field data for one of the predetermined segments to which at least one of the two or more segments is most similar is assigned to the at least one of the two or more segments. In other words, when a reticle is being inspected, its pattern information can be separated into segments, compared to the predetermined segments in the library, and the near-field data in the library for a predetermined segment can be assigned to the segment that it matches. These steps may be performed as described further herein.

In this manner, setting up the reticle inspection process as described herein may include generating a library that will be used in a reticle inspection process and at least making that library available for use in the reticle inspection process. However, the embodiments described herein may or may not include setting up other parameters (e.g., optical parameters, defect detection parameters, etc.) of a reticle inspection process. For example, the other parameters can be determined in some other method or with some other system and the information for the library (e.g., a link to the library and/or an ID for the library) can be incorporated into the process. As such, the embodiments described herein may include setting up only one element (the library) of an entire reticle inspection process. The recipe for the reticle inspection process can be any set of instructions that can be used by a reticle inspection system to perform the reticle inspection process. Such instructions may have any suitable format and may be stored in any suitable data structure.

The separating, determining, generating, and setting up steps are performed by one or more computer systems, which may be configured according to any of the embodiments described herein.

Each of the embodiments of the methods described above may include any other step(s) of any other method(s) described herein. Furthermore, each of the embodiments of the methods described above may be performed by any of the systems described herein.

An additional embodiment of a computer-implemented method for setting up a reticle inspection process includes the separating, generating, and setting up steps described above. However, this embodiment does not necessarily include the determining step described above, Instead, in this embodiment, the method includes determining near-field data for the predetermined segments by numerically solving equations that govern electromagnetic fields for the predetermined segments. In other words, the embodiments may use Maxwell's equations to determine the near-field for different predetermined segments. The near-fields determined from Maxwell's equations and their corresponding predetermined segments can then be stored in a data structure (e.g., library) as described further herein. Those near-field and predetermined segment pairs can then be used during a reticle inspection process as described further herein. The equations that govern the electromagnetic fields for the predetermined segments (or the Maxwell's equations) can be solved in any suitable manner using any suitable method and/or algorithm.

The separating, determining, generating, and setting up steps are performed by one or more computer systems, which may be configured according to any of the embodiments described herein.

Each of the embodiments of the methods described above may include any other step(s) of any other method(s) described herein. Furthermore, each of the embodiments of the methods described above may be performed by any of the systems described herein.

Another embodiment relates to a computer-implemented method for detecting defects on a reticle. In other words, this embodiment may include inspecting a reticle or performing a reticle inspection process on a reticle. The reticle inspection process performed in the embodiments described further herein may be set up (at least in part) as described above.

As shown in step 108 of FIG. 1, this method includes separating a pattern included in an inspection area on the reticle into two or more segments. For example, given an inspection area of a reticle, the database for that inspection area can be divided or broken up into relatively small segments. The method may or may not include selecting the inspection area on the reticle. For example, the inspection area on the reticle may be determined by another method or system, and information for the inspection area may be included in a recipe for a reticle inspection process. The two or more segments may be configured as described further herein.

As shown in step 110 of FIG. 1, the method also includes separately comparing the two or more segments to predetermined segments included in a data structure. The data structure includes pairs of predetermined segments of a reticle pattern and corresponding near-field data. In this manner, each segment of the database may be looked up in the library. In particular, the separately comparing step may include seeking a match for a section of the database for a reticle being inspected from among the database segments in the library. In other words, this step may include finding a matching pattern in the library.

In one embodiment, diameters of the two or more segments are larger than an optical proximity distance for the reticle. For example, as described above, the reticle pattern may be separated into relatively small segments or sections. Then, a match for this section of the database may be searched for among the database segments in the library. To increase the probability of finding a match, a relatively small section of the database may be processed at a time. However, the diameter of the section should be larger than the optical proximity distance.

In one embodiment, the method includes determining the pairs of the predetermined segments and the corresponding near-field data by separating pattern information for the reticle or another reticle into the predetermined segments and determining the near-field data for the predetermined segments based on one or more actual images of the reticle or the other reticle acquired by the detector or another detector. These steps may be performed as described further herein. For example, the library that is used for the embodiments described herein may be created as described above.

In one such embodiment, the near-field data for the predetermined segments is determined by regression based on the one or more actual images of the reticle or the other reticle. The near-field data may be determined in this manner as described in further detail herein.

In an additional embodiment, the method includes determining the pairs of the predetermined segments and the corresponding near-field data by separating pattern information for the reticle or another reticle into the predetermined segments and determining the near-field data for the predetermined segments by numerically solving equations that govern electromagnetic fields for the predetermined segments of the reticle pattern. These steps may be performed as described further herein. For example, the library that is used for the embodiments described herein may be created as described above.

In another embodiment, separately comparing the two or more segments to the predetermined segments includes comparing gray scale images for the two or more segments to gray scale images for the predetermined segments. For example, finding a match in the library may involve evaluating the correlation of gray scale rasterized database images. In an additional embodiment, separately comparing the two or more segments to the predetermined segments includes comparing coordinates of vertices of polygons in one of the two or more segments to coordinates of vertices of polygons in the predetermined segments, and a solid-body translation of the coordinates of the vertices in the one of the two or more segments and the predetermined segments is not considered a difference during the separately comparing. For example, if the database contains coordinates of vertices of polygons, the coordinates of the vertices can be matched up to an arbitrary translation. Such separately comparing steps may be performed in any suitable manner using any suitable method and/or algorithm.

As shown in step 112 of FIG. 1, the method further includes assigning near-field data to at least one of the two or more segments based on one of the predetermined segments to which the at least one of the two or more segments is most similar. Assigning the near-field data to the at least one segment may include retrieving the near-field from the library that corresponds to the predetermined segment to which it is most similar. The retrieved near-field can then be assigned to a point in the inspection area. Determining how similar the segments of a reticle being inspected are to the predetermined segments in the library may be performed in any suitable manner using any suitable algorithm and/or method. In this manner, the near-field of the reticle may be calculated by looking it up in the library during inspection.

In one embodiment, when the one of the predetermined segments to which the at least one of the two or more segments is most similar is not an exact match for the at least one of the two or more segments, assigning the near-field data to the at least one of the two or more segments includes determining a mapping of the one of the predetermined segments to the at least one of the two or more segments, applying the mapping to the near-field data corresponding to the one of the predetermined segments to generate modified near-field data, and assigning the modified near-field data to the at least one of the two or more segments. In this manner, if an exact match is not found, the closest match in the library may be selected. In one such implementation, a morphological operation may be found that maps the library database segment to the database section of the inspection region. The same morphological operation may then be applied to the library near-field. For example, suppose we are looking for the near-field of a 54 nm wide line in a clear field, but the closest match in the library is a 50 nm wide line. The map of the near-field of the 50 nm wide line may be selected and stretched to cover the 54 nm wide line.

In another embodiment, when one of the predetermined segments to which at least one other of the two or more segments is most similar cannot be found for the at least one other of the two or more segments, the method includes determining near-field data for the at least one other of the two or more segments based on the actual image generated by the detector and adding the determined near-field data to the data structure. For example, if no match can be found, a near-field recovery may be performed as described herein and its result can be included in the library.

As shown in step 114 of FIG. 1, the method includes generating near-field data for the inspection area based on the assigned near-field data. For example, generating the near-field data for the inspection area may include making a collage of retrieved near-fields so that a single near-field value is assigned to each point of the inspection area. In this manner, an image may be calculated from the assigned near-fields.

In one embodiment, the method also includes simulating an image, based on the generated near-field data, of the inspection area that would be formed by a detector of a reticle inspection system. For example, the assigned near-field values may be propagated to the detector array using Hopkins or Gamo-Gabor theory, and an image intensity may be determined.

As shown in step 116 of FIG. 1, the method further includes acquiring an actual image of the inspection area on a physical version of the reticle generated by the detector. In this manner, an optical image of the region to be inspected may be acquired. An actual image of the inspection area on a physical version of the reticle may be generated as described further herein using any detector(s) of any systems described herein.

As shown in step 118 of FIG. 1, the method also includes detecting defects on the reticle by comparing the simulated image to the actual image. For example, the acquired optical image may be compared to the computed image intensity, and significant differences between the calculated image and the acquired optical image of the inspection area may be detected and reported. Detecting the defects on the reticle based on results of comparing the simulated image to the actual image may, however, be performed in any other suitable manner using any other suitable method and/or algorithm.

The embodiments described herein have, therefore, a number of advantages over other currently used reticle inspection methods. For example, recovering the near-field of a reticle from its optical images as described further herein is faster than solving Maxwell's equations. In addition, creating a library of recovered near-fields and collaging near-fields retrieved from the library reduces the number of near-field recovery calculations.

In a further embodiment, the method includes simulating one or more characteristics of patterned features that would be formed on a wafer in a process performed with the reticle by inputting the generated near-field data into a model, measuring the one or more characteristics of the patterned features that have been formed on the wafer in the process, comparing the simulated one or more characteristics to the measured one or more characteristics, and altering one or more parameters of the model based on results of the comparing step. In this manner, a lithographic imaging model may be applied to the mask near-field to predict a lithographic image. As such, the method may include predicting a critical dimension on a wafer or an outcome of lithography using the predicted lithographic image. In addition, a computational model of lithography can be calibrated using the recovered near-field and wafer images (e.g., wafer scanning electron microscope (SEM) images). In other words, the embodiments described herein can calibrate modeling parameters in a litho process, which are critical to predicting wafer patterns, from a set of LNI images.

In some such embodiments, the reticle whose images are used to determine the near-field data that is input into a model may be a calibration mask. This calibration mask may include a set of one-dimensional (1D) and 2D patterns. The mask can be the same one that is used to generate an OPC model. Alternatively, the mask can be designed by a reticle inspection tool supplier such as KLA-Tencor, Milpitas, Calif.

A set of LNI images may be acquired for the calibration mask as described herein. The imaging conditions used to acquire these image(s) are preferably such that the illumination source shape and NA on the objective side are identical or nearly identical to those on a scanner. The LNI images can be through-focus for the purpose of better conditioning the subsequent calculations. An alternative method is to acquire a set of LNI images with nearly coherent illumination conditions but with different incident angles.

The mask near-field (or MNR) may then be recovered as described further herein. For example, with a set of LNI images with known illumination and imaging conditions, the mask-plane amplitude and phase information can be reconstructed iteratively through an objective function that minimizes the difference between the acquired LNI images and images calculated from the mask near-field.

The lithographic process can then be modeled. For example, the mask near-field may be fed to a computation engine to generate the wafer-level images. The computation engine preferably includes the scanner imaging process through photoresist materials that explicitly consider polarization and vector imaging effects. The engine preferably also contains the photoresist development process including acid and base diffusion and base quenching, for example. The computation engine can also optionally include the etch modeling.

The simulated wafer images may then be compared with experimentally acquired SEM images for a wafer printed with the same calibration mask. Any differences between the simulated wafer images and the experimentally acquired images can be used to adjust model parameters iteratively to thereby reduce image differences (e.g., such that the simulated wafer images substantially match the experimentally acquired images). This iterative process enables the extraction of lithography model parameters. The embodiments described herein therefore provide a calibration procedure to extract lithography model parameters. In addition, the embodiments described herein combine mask near-field with a full lithography model and a calibration mask to extract lithography model parameters. These model parameters can then be stored and retrieved later when a defect is found.

The embodiments described herein for calibrating a lithography model provide a number of advantages over currently used methods and systems for calibrating lithography models. For example, currently used methods for calibrating lithography models are based on inaccurate methods of solving Maxwell's equations. In addition, some currently used methods assume a database of geometric shapes represents the actual pattern on the reticle. Furthermore, some currently used methods assume a preselected three-dimensional (3D) profile represents the actual profile etched in the reticle. Moreover, some currently used methods assume a set of material parameters represents the materials that make up the reticle. Additional disadvantages of currently used methods and systems are described in the background section of this document.

Defects detected by reticle inspections are relatively difficult to disposition in terms of their printability due to increased OPC complexity. Simple resist threshold models are not adequate for LNI images or aerial images. A resist model calibration on top of a scanning imaging model is needed to accurately predict the wafer-level impact of a defect before a wafer is actually printed using a physical scanner. As such, it is highly desirable to construct new methods that can be used to substantially accurately predict the wafer-level behaviors of a defect before a reticle is shipped to a wafer fab.

In one such embodiment, the method includes, for at least one of the defects detected on the reticle, determining near-field data for the at least one of the defects based on the actual image of the at least one of the defects and simulating how the at least one of the defects would be printed on the wafer in the process by inputting the determined near-field data for the at least one of the defects into the model. In this manner, the method may include substantially accurate wafer-level defect printability with reticle inspection images. In other words, the embodiments may be used to analyze the reticle defect printability. For example, once a defect is detected on a reticle, a set of LNI images can be acquired at or near the defect, these images can be used to recover the mask near-field for the defect, which can be performed as described herein, and lithography modeling, with the modeling parameters extracted through the embodiments described herein, can be performed to calculate the defect behavior accurately on the wafer. In addition, once a simulated image illustrating how the at least one defect will print on a wafer has been acquired using a model calibrated as described herein, that simulated image can be compared to information for how the area of the reticle was intended to be printed on the wafer (which can be acquired from a pre-OPC database for the reticle). As such, the reticle defect printing impact on a wafer can be calculated using a pre-OPC database. Therefore, how the reticle defect will alter the printing of the reticle on the wafer from its intended printing can be determined by comparing calculated wafer-level image(s) with a pre-OPC database to predict defect behavior.

The embodiments described herein can be used to qualify reticles and accurately predict the wafer-level impact or behavior of defects on reticles before the reticles are shipped to the fab and before high-volume manufacturing is performed with the reticles. Subsequent defect disposition can be performed to separate a critical defect from a non-critical defect. For example, once the effect of the defect on the printing of the reticle on the wafer has been determined, the defect can be dispositioned or classified accordingly (e.g., as a non-printing defect, a printing defect, a critical printing defect (e.g., one that will affect yield), a non-critical printing defect (e.g., a defect that will print but not affect yield), etc.).

The defect printability embodiments described herein have, therefore, a number of advantages over other methods and systems used for predicting defect printability. For example, the embodiments described herein may be performed using lithography models that include scanning imaging characteristics and photoresist development processes. In addition, the combination of mask near-field recovery and lithography model calibration (e.g., combining inspection images and lithography process steps to calibrate lithography models) leads to more accurate wafer-level predictions from inspection images. Therefore, the embodiments described herein provide calibration results that can be used to substantially accurately predict wafer-level behaviors of a defect for printability analyses.

The calibration steps described herein can be implemented on existing reticle inspection tools. In addition, defect disposition with the calibrated model can be implemented on existing reticle inspection tools.

The separating, separately comparing, assigning, generating, simulating, acquiring, and detecting steps are performed with one or more computer systems, which may be configured according to any of the embodiments described herein.

Each of the embodiments of the methods described above may include any other step(s) of any other method(s) described herein. Furthermore, each of the embodiments of the methods described above may be performed by any of the systems described herein.

All of the methods described herein may include storing results of one or more steps of the method embodiments in a computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc.

Figure 2:
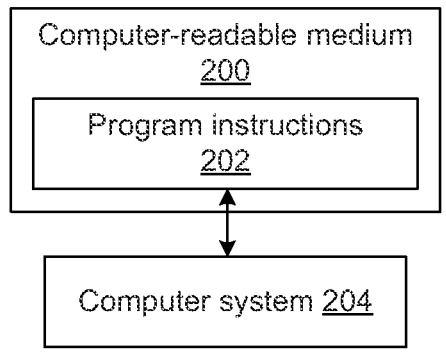
FIG. 2 is a block diagram illustrating one embodiment of a non-transitory computer-readable medium storing program instructions for causing a computer system to perform one or more of the computer-implemented methods described herein.

Another embodiment relates to a non-transitory computer-readable medium storing program instructions executable on a computer system for performing one or more of the computer-implemented methods described herein. One such embodiment is shown in FIG. 2. For example, as shown in FIG. 2, non-transitory computer-readable medium 200 stores program instructions 202 executable on computer system 204 for performing one or more of the computer-implemented methods described herein. The computer-implemented method(s) may include any step(s) of any method(s) described herein.

Program instructions 202 implementing methods such as those described herein may be stored on non-transitory computer-readable medium 200. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

Computer system 204 may take various forms, including a personal computer system, mainframe computer system, workstation, system computer, image computer, programmable image computer, parallel processor, or any other device known in the art. In general, the term "computer system" may be broadly defined to encompass any device having one or more processors, which executes instructions from a memory medium.

In one embodiment, the computer system described above may include one or more computer subsystems that are part of an electronic design automation (EDA) tool (not shown), and the reticle inspection system described further herein is not part of the EDA tool. The EDA tool and the computer subsystem(s) included in such a tool may include any commercially available EDA tool that can be configured to perform one or more of the steps described above. For instance, the computer subsystem(s) that are configured to separate the pattern included in an inspection area on the reticle into segments may be part of an EDA tool. In this manner, the design data for a reticle may be processed by the EDA tool to separate the pattern into segments that will be used by another, different system or tool as described herein.

The computer subsystem(s) also may not be part of an EDA tool and may be included in another system or tool or simply be configured as stand-alone computer system(s). Furthermore, the tool or computer subsystem that separates a pattern into segments, generates a data structure, and/or sets up a reticle inspection process as described herein may be configured to provide that information to another tool or computer subsystem by storing or transferring information generated by such steps to a shared computer-readable storage medium such as a fab database or by transmitting the information directly to the tool that will use it.

Figure 3:
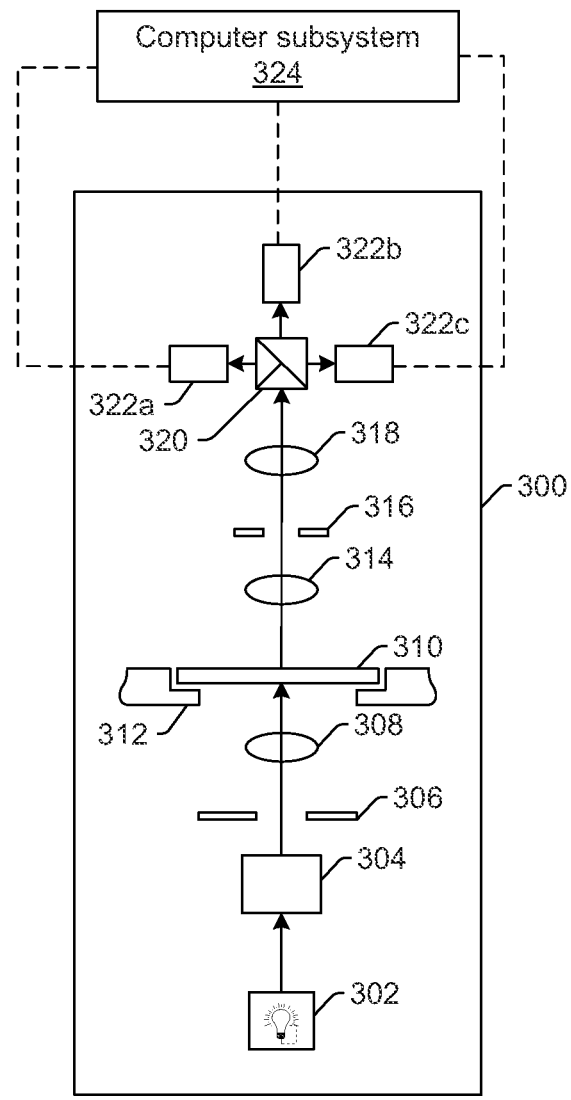
FIG. 3 is a schematic diagram illustrating a side view of an embodiment of a system configured to detect defects on a reticle.

Another embodiment relates to a system configured to detect defects on a reticle. One embodiment of such a system is shown in FIG. 3. The system includes a reticle inspection subsystem that includes a detector configured to generate an actual image of an inspection area on a physical version of the reticle. The actual image may be any of such images described further herein. As shown in FIG. 3, the system includes reticle inspection subsystem 300.

As further shown in FIG. 3, reticle inspection subsystem 300 includes an illumination subsystem and a collection subsystem as described in more detail herein. The illumination subsystem includes light source 302. Light source 302 may be a coherent light source such as a laser. The light source may be configured to emit monochromatic light having a wavelength of about 248 nm, about 193 nm, about 157 nm, or another ultraviolet wavelength. Alternatively, the light source may be configured to emit light have a range of wavelengths and may be coupled to a spectral filter (not shown). An example of a broadband light source includes, but is not limited to, a He—Xe arc lamp that generates light in the deep ultraviolet wavelength regime. In this manner, the light source and the filter may emit monochromatic light having a wavelength as described above. The light source and the filter may be configured such that different wavelengths of light may be emitted from the light source and the filter depending upon, for example, the type of reticle being inspected or the type of inspection or measurement being performed. The light source may also be configured to emit light other than ultraviolet light. In addition, the light source may be configured to emit light continuously or at various time intervals in pulses.

The illumination subsystem may also include a number of optical components coupled to the light source. For example, light from light source 302 may first pass through homogenizer 304. Homogenizer 304 may be configured to reduce speckle of the light from the light source. The illumination subsystem may also include aperture 306. Aperture 306 may have an adjustable NA. For example, the aperture may be coupled to a control mechanism that may be configured to mechanically alter the aperture depending upon a control signal received from a user or from program instructions received from a program recipe being run on the system. In this manner, the light may have various partial coherence factors, $\sigma$. For example, aperture 306 may be altered to adjust a pupil of condenser lens 308. The pupil of the condenser lens controls the NA of the system. As the pupil of the condenser is reduced, coherence of the illumination increases thereby decreasing the value of $\sigma$. The value of $\sigma$ may be expressed as the ratio of the NA of the condenser lens to the NA of the objective lens. Exposure systems may have a value of $\sigma$ in a range between about 0.3 to about 0.9. Therefore, aperture 306 may be altered such that the optical subsystem has a value of $\sigma$ between about 0.3 and about 0.9. The value of $\sigma$ may be altered depending upon the features on the reticle. For example, a higher value for $\sigma$ may be used if the reticle includes lines and spaces than if the reticle includes contact holes. The control mechanism may also be configured to alter the aperture to provide annular or off-axis illumination. The aperture may also be configured to provide other types of illumination such as quadrapole or dipolar illumination. The aperture may be further configured to alter a shape of the beam of light. For example, the aperture may be a diffraction optical element or an apodization aperture.

The illumination subsystem may also include a number of additional optical components (not shown). For example, the illumination subsystem may also include a telescope configured to alter the beam diameter of the light. In addition, the illumination subsystem may include one or more relay lenses, additional lenses such as a field lens, folding mirrors, additional apertures, and beamsplitters.

The illumination subsystem may also include condenser lens 308. Condenser lens 308 may be configured to alter a diameter of the light in the object (reticle) plane to approximately, or greater than, the field of view of the system. Light exiting the condenser lens may illuminate reticle 310 supported upon stage 312. The stage is configured to support the reticle by contacting the reticle proximate outer lateral edges of the reticle. An opening in the stage is provided to allow light from the illumination subsystem to illuminate the reticle. Stage 312 may be configured to move the reticle such that an alignment of the reticle may be altered and such that light may scan across the reticle. Alternatively, the illumination subsystem may include a scanning element (not shown) such as an acousto-optical deflector or a mechanical scanning assembly such that the reticle may remain substantially stationary while the light is scanned across the reticle. Stage 312 may also be configured to move the reticle through focus thereby altering a focus setting of the optical subsystem. The stage may also be coupled to an autofocusing device (not shown) that is configured to alter a position of the stage thereby altering a position of the reticle to maintain a focus setting of the optical subsystem during an inspection. Alternatively, an autofocusing device may be coupled to the objective lens to alter a position of the objective lens to maintain the focus setting during an inspection.

The optical subsystem may also include a number of optical components arranged to form a collection subsystem. For example, the collection subsystem includes objective lens 314. Light transmitted by the reticle is collected by objective lens 314. The collection subsystem also includes aperture 316 having an adjustable NA. The NA of aperture 316 may also be selected such that light exiting the aperture has a selected magnification. Aperture 316 is positioned between objective lens 314 and lens 318, which may be configured as a tube lens. Light from lens 318 may be directed to beamsplitter 320. Beamsplitter 320 may be configured to direct the light to three detectors 322a, 322b, and 322c. The collection subsystem may also include a number of additional optical components (not shown) such as a magnification lens. The magnification lens may be positioned between lens 318 and the beamsplitter.

Detectors 322a, 322b, and 322c may be configured to form an image of the light transmitted by an illuminated portion of the reticle. Such an image may be referred to as an "aerial image." The detectors should also be sensitive to at least one of the wavelengths of light described above. The detectors, however, may also be sensitive to a range of wavelengths in the deep ultraviolet regime in addition to wavelengths in other regimes. The detectors may include, for example, charge coupled devices (CCDs) or time delay integration (TDI) cameras. The detectors may also have a one-dimensional or two-dimensional array of pixels. Each of the three detectors may have a different focus setting. In this manner, the three detectors may form images of the reticle at three different focus settings substantially simultaneously. For example, one detector may be substantially in focus, and the other two detectors may be out of focus in opposite directions with respect to the in-focus condition. In addition, the reticle inspection subsystem may include any number of such detectors depending on the mechanical or physical constraints of the reticle inspection subsystem.

Alternatively, the reticle inspection subsystem may only include one detector configured to generate an actual image of the reticle. The detector may have a focus setting approximately equal to a focus setting of an exposure system. Images of the reticle at different focus settings may be formed by forming a plurality of images of the reticle and altering the focus setting of the detector after each image is formed. In such an embodiment, beamsplitter 320 would not be necessary to split the light to multiple detectors.

The reticle inspection subsystem may include a number of other components that are not shown in FIG. 3. For example, the system may include a load module, an alignment module, a handler such as a robotic transfer arm, and an environmental control module and may include any such components known in the art.

As described above, the reticle inspection subsystem may be configured to form an aerial image of the reticle using a set of exposure conditions. The exposure conditions include, but are not limited to, wavelength of illumination, coherence of illumination, shape of the beam of illumination. NA, and focus settings. The set of exposure conditions may be selected to be substantially equivalent to exposure conditions used by an exposure system to print an image of the reticle onto a wafer. Therefore, an aerial image formed by reticle inspection subsystem 300 may be substantially optically equivalent to an image of the reticle that would be printed on a wafer by the exposure system under the set of exposure conditions.

The system also includes one or more computer subsystems configured for performing one or more steps of one or more of the computer-implemented methods described herein. In one embodiment, as shown in FIG. 3, the system includes computer subsystem 324. In the embodiment shown in FIG. 3, computer subsystem 324 is coupled to reticle inspection subsystem 300. For example, the computer subsystem may be coupled to a detector of the reticle inspection subsystem. In one such example, as shown in FIG. 3, computer subsystem 324 is coupled to detectors 322a, 322b, and 322c of reticle inspection subsystem 300 (e.g., by one or more transmission media shown by the dashed lines in FIG. 3, which may include any suitable transmission media known in the art). The computer subsystem may be coupled to the detectors in any suitable manner. The computer subsystem may be coupled to the reticle inspection subsystem in any other suitable manner such that image(s) and any other information for the reticle generated by the reticle inspection subsystem can be sent to the computer subsystem and, optionally, such that the computer subsystem can send instructions to the reticle inspection subsystem to perform one or more steps described herein. The computer subsystem(s) included in the system may also be further configured as described herein.

It is noted that FIG. 3 is provided herein to generally illustrate one configuration of a reticle inspection subsystem that may be included in the system embodiments described herein. Obviously, the configuration of the reticle inspection subsystems described herein may be altered to optimize the performance of the system as is normally performed when designing a commercial inspection system. In addition, the systems described herein may be implemented using an existing reticle inspection subsystem (e.g., by adding functionality described herein to an existing inspection system) such as the reticle inspection tools that are commercially available from KLA-Tencor. For some such systems, the methods described herein may be provided as optional functionality of the system (e.g., in addition to other functionality of the system). Alternatively, the reticle inspection systems described herein may be designed "from scratch" to provide a completely new system.

Further modifications and alternative embodiments of various aspects of the invention will be apparent to those skilled in the art in view of this description. For example, systems and methods for detecting defects on a reticle are provided. Accordingly, this description is to be construed as illustrative only and for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for detecting defects on a reticle, comprising:

separating a pattern included in an inspection area on the reticle into two or more segments;

separately comparing the two or more segments to predetermined segments included in a data structure, wherein the data structure comprises pairs of the predetermined segments of a reticle pattern and corresponding near-field data;

assigning near-field data to at least one of the two or more segments based on one of the predetermined segments to which the at least one of the two or more segments is most similar;

generating near-field data for the inspection area based on the assigned near-field data;

simulating an image, based on the generated near-field data, of the inspection area that would be formed by a detector of a reticle inspection system;

acquiring an actual image of the inspection area on a physical version of the reticle generated by the detector; and detecting defects on the reticle by comparing the simulated image to the actual image, wherein said separating, separately comparing, assigning, generating, simulating, acquiring, and detecting are performed with one or more computer systems.

2. The method of claim 1, further comprising determining the pairs of the predetermined segments and the corresponding near-field data by separating pattern information for the reticle or another reticle into the predetermined segments and determining the near-field data for the predetermined segments based on one or more actual images of the reticle or the other reticle acquired by the detector or another detector.

3. The method of claim 2, wherein the pattern information is acquired from design data for the reticle.

4. The method of claim 2, further comprising selecting the predetermined segments from the pattern information based on number of instances of the predetermined segments in an entirety of the pattern for the reticle.

5. The method of claim 2, wherein the one or more actual images of the reticle or the other reticle are acquired at more than one focus setting by the detector or the other detector.

6. The method of claim 2, wherein the near-field data for the predetermined segments is determined by regression based on the one or more actual images of the reticle or the other reticle.

7. The method of claim 6, wherein the regression comprises a Hopkins phase approximation.

8. The method of claim 6, wherein the regression does not comprise thin-mask approximations.

9. The method of claim 6, wherein the regression does not comprise Kirchhoff approximations.

10. The method of claim 1, further comprising determining the pairs of the predetermined segments and the corresponding near-field data by separating pattern information for the reticle or another reticle into the predetermined segments and determining the near-field data for the predetermined segments by numerically solving equations that govern electromagnetic fields for the predetermined segments of the reticle pattern.

11. The method of claim 10, wherein the pattern information is acquired from design data for the reticle.

12. The method of claim 10, further comprising selecting the predetermined segments from the pattern information based on number of instances of the predetermined segments in an entirety of the pattern for the reticle.

13. The method of claim 1, wherein diameters of the two or more segments are larger than an optical proximity distance for the reticle.

14. The method of claim 1, wherein said separately comparing comprises comparing gray scale images for the two or more segments to gray scale images for the predetermined segments.

15. The method of claim 1, wherein said separately comparing comprises comparing coordinates of vertices of polygons in one of the two or more segments to coordinates of vertices of polygons in the predetermined segments, and wherein a solid-body translation of the coordinates of the vertices in the one of the two or more segments and the predetermined segments is not considered a difference during said separately comparing.

16. The method of claim 1, wherein when the one of the predetermined segments to which the at least one of the two or more segments is most similar is not an exact match for the at least one of the two or more segments, assigning the near-field data to the at least one of the two or more segments comprises determining a mapping of the one of the predetermined segments to the at least one of the two or more segments, applying the mapping to the near-field data corresponding to the one of the predetermined segments to generate modified near-field data, and assigning the modified near-field data to the at least one of the two or more segments.

17. The method of claim 1, wherein when one of the predetermined segments to which at least one other of the two or more segments is most similar cannot be found for the at least one other of the two or more segments, the method further comprises determining near-field data for the at least one other of the two or more segments based on the actual image generated by the detector and adding the determined near-field data to the data structure.

18. The method of claim 1, further comprising simulating one or more characteristics of patterned features that would be formed on a wafer in a process performed with the reticle by inputting the generated near-field data into a model, measuring the one or more characteristics of the patterned features that have been formed on the wafer in the process, comparing the simulated one or more characteristics to the measured one or more characteristics, and altering one or more parameters of the model based on results of said comparing.

19. The method of claim 18, further comprising, for at least one of the defects detected on the reticle, determining near-field data for the at least one of the defects based on the actual image of the at least one of the defects and simulating how the at least one of the defects would be printed on the wafer in the process by inputting the determined near-field data for the at least one of the defects into the model.

20. A computer-implemented method for setting up a reticle inspection process, comprising:

separating pattern information for a reticle into predetermined segments;

determining near-field data for the predetermined segments based on one or more actual images of the reticle acquired by a detector of a reticle inspection system, wherein the near-field data for the predetermined segments is determined by regression based on the one or more actual images of the reticle;

generating a data structure that comprises pairs of the predetermined segments and the near-field data corresponding to the predetermined segments; and setting up the reticle inspection process by incorporating information for the generated data structure in a recipe for the reticle inspection process such that during the reticle inspection process, two or more segments in an inspection area on the reticle or another reticle are compared to the predetermined segments and the near-field data for one of the predetermined segments to which at least one of the two or more segments is most similar is assigned to the at least one of the two or more segments, wherein the separating, determining, generating, and setting up steps are performed by one or more computer systems.

21. A computer-implemented method for setting up a reticle inspection process, comprising:

separating pattern information for a reticle into predetermined segments;

determining near-field data for the predetermined segments by numerically solving equations that govern electromagnetic fields for the predetermined segments;

generating a data structure that comprises pairs of the predetermined segments and the near-field data corresponding to the predetermined segments; and setting up the reticle inspection process by incorporating information for the generated data structure in a recipe for the reticle inspection process such that during the reticle inspection process, two or more segments in an inspection area on the reticle or another reticle are compared to the predetermined segments and the near-field data for one of the predetermined segments to which at least one of the two or more segments is most similar is assigned to the at least one of the two or more segments, wherein the separating, determining, generating, and setting up steps are performed by one or more computer systems.

22. A non-transitory computer-readable medium, storing program instructions executable on a computer system for performing a computer-implemented method for detecting defects on a reticle, wherein the computer-implemented method comprises:

separating a pattern included in an inspection area on the reticle into two or more segments;

separately comparing the two or more segments to predetermined segments included in a data structure, wherein the data structure comprises pairs of the predetermined segments of a reticle pattern and corresponding near-field data;

assigning near-field data to at least one of the two or more segments based on one of the predetermined segments to which the at least one of the two or more segments is most similar;

generating near-field data for the inspection area based on the assigned near-field data;

simulating an image, based on the generated near-field data, of the inspection area that would be formed by a detector of a reticle inspection system;

acquiring an actual image of the inspection area on a physical version of the reticle generated by the detector; and detecting defects on the reticle by comparing the simulated image to the actual image.

23. A system configured to detect defects on a reticle, comprising:

a reticle inspection subsystem comprising a detector configured to generate an actual image of an inspection area on a physical version of the reticle; and one or more computer subsystems configured for:

separating a pattern included in the inspection area into two or more segments;

separately comparing the two or more segments to predetermined segments included in a data structure, wherein the data structure comprises pairs of the predetermined segments of a reticle pattern and corresponding near-field data;

assigning near-field data to at least one of the two or more segments based on one of the predetermined segments to which the at least one of the two or more segments is most similar;

generating near-field data for the inspection area based on the assigned near-field data;

simulating an image, based on the generated near-field data, of the inspection area that would be formed by the detector;

acquiring the actual image from the detector; and detecting defects on the reticle by comparing the simulated image to the actual image.

24. The system of claim 23, wherein the one or more computer subsystems are further configured for determining the pairs of the predetermined segments and the corresponding near-field data by separating pattern information for the reticle or another reticle into the predetermined segments and determining the near-field data for the predetermined segments based on one or more actual images of the reticle or the other reticle acquired by the detector or another detector.

25. The system of claim 24, wherein the pattern information is acquired from design data for the reticle.

26. The system of claim 24, wherein the one or more computer subsystems are further configured for selecting the predetermined segments from the pattern information based on number of instances of the predetermined segments in an entirety of the pattern for the reticle.

27. The system of claim 24, wherein the one or more actual images of the reticle or the other reticle are acquired at more than one focus setting by the detector or the other detector.

28. The system of claim 24, wherein the near-field data for the predetermined segments is determined by regression based on the one or more actual images of the reticle or the other reticle.

29. The system of claim 28, wherein the regression comprises a Hopkins phase approximation.

30. The system of claim 28, wherein the regression does not comprise thin-mask approximations.

31. The system of claim 28, wherein the regression does not comprise Kirchhoff approximations.

32. The system of claim 23, wherein the one or more computer subsystems are further configured for determining the pairs of the predetermined segments and the corresponding near-field data by separating pattern information for the reticle or another reticle into the predetermined segments and determining the near-field data for the predetermined segments by numerically solving equations that govern electromagnetic fields for the predetermined segments of the reticle pattern.

33. The system of claim 32, wherein the pattern information is acquired from design data for the reticle.

34. The system of claim 32, wherein the one or more computer subsystems are further configured for selecting the predetermined segments from the pattern information based on number of instances of the predetermined segments in an entirety of the pattern for the reticle.

35. The system of claim 23, wherein diameters of the two or more segments are larger than an optical proximity distance for the reticle.

36. The system of claim 23, wherein said separately comparing comprises comparing gray scale images for the two or more segments to gray scale images for the predetermined segments.

37. The system of claim 23, wherein said separately comparing comprises comparing an arbitrary translation of coordinates of vertices of polygons in the two or more segments and coordinates of vertices of polygons in the predetermined segments.

38. The system of claim 23, wherein when the one of the predetermined segments to which the at least one of the two or more segments is most similar is not an exact match for the at least one of the two or more segments, assigning the near-field data to the at least one of the two or more segments comprises determining a mapping of the one of the predetermined segments to the at least one of the two or more segments, applying the mapping to the near-field data corresponding to the one of the predetermined segments to generate modified near-field data, and assigning the modified near-field data to the at least one of the two or more segments.

39. The system of claim 23, wherein when one of the predetermined segments to which at least one other of the two or more segments is most similar cannot be found for the at least one other of the two or more segments, the one or more computer subsystems are further configured for determining near-field data for the at least one other of the two or more segments based on the actual image generated by the detector and adding the determined near-field data to the data structure.

40. The system of claim 23, wherein the one or more computer subsystems are further configured for simulating one or more characteristics of patterned features that would be formed on a wafer in a process performed with the reticle by inputting the generated near-field data into a model, measuring the one or more characteristics of the patterned features that have been formed on the wafer in the process, comparing the simulated one or more characteristics to the measured one or more characteristics, and altering one or more parameters of the model based on results of said comparing.

41. The system of claim 40, wherein the one or more computer subsystems are further configured for, for at least one of the defects detected on the reticle, determining near-field data for the at least one of the defects based on the actual image of the at least one of the defects and simulating how the at least one of the defects would be printed on the wafer in the process by inputting the determined near-field data for the at least one of the defects into the model.

* * * * *